United States Patent [19]

Bilstad et al.

[11] Patent Number: 4,605,503

[45] Date of Patent: Aug. 12, 1986

[54] SINGLE NEEDLE BLOOD FRACTIONATION SYSTEM HAVING ADJUSTABLE RECIRCULATION THROUGH FILTER

[75] Inventors: Arnold C. Bilstad, Deerfield; Richard I. Brown, Northbrook; Robert J. Kruger, Arlington Heights, all of Ill.

[73] Assignee: Baxter Travenol Laboratories, Inc., Deerfield, Ill.

[21] Appl. No.: 498,581

[22] Filed: May 26, 1983

[51] Int. Cl.$^4$ .............................................. B01D 13/00
[52] U.S. Cl. ................................. 210/651; 210/433.2; 604/6
[58] Field of Search ............................ 422/46; 604/6; 210/321.1, 433.2, 927, 651

[56] References Cited

U.S. PATENT DOCUMENTS

| | | | |
|---|---|---|---|
| 3,472,765 | 10/1969 | Budd et al. | 210/7 |
| 3,567,031 | 3/1971 | Loeffler | 210/433.2 X |
| 3,682,172 | 8/1972 | Freedman et al. | 210/321.1 X |
| 3,699,960 | 10/1972 | Freedman | 210/321.1 X |
| 3,705,100 | 12/1972 | Blatt et al. | 210/321.1 X |
| 3,802,432 | 4/1974 | Djerassi | 128/214 R |
| 3,890,969 | 6/1975 | Fischel | 422/46 X |
| 3,927,980 | 12/1975 | Leonard | 422/48 |
| 3,953,329 | 4/1976 | Updike | 210/22 R |
| 3,967,777 | 7/1976 | Canevari | 233/31 X |
| 4,013,564 | 3/1977 | Nose | 210/434 |
| 4,026,669 | 5/1977 | Leonard et al. | 128/DIG. 3 |
| 4,191,182 | 3/1980 | Popovich et al. | 210/433.2 X |
| 4,209,392 | 6/1980 | Wallace | 210/321.2 |
| 4,343,705 | 8/1982 | Legg | 210/443 X |
| 4,447,191 | 5/1984 | Bilstad et al. | 604/6 X |

FOREIGN PATENT DOCUMENTS

| | | | |
|---|---|---|---|
| 0044694 | 1/1982 | European Pat. Off. | 210/927 |
| 79/01121 | 12/1979 | PCT Int'l Appl. | 210/927 |

OTHER PUBLICATIONS

Bilstad et al., "Blood Fractionation Apparatus", International Publication No. WO81/02979, 10-1981.

*Primary Examiner*—Frank Spear
*Attorney, Agent, or Firm*—Eugene M. Cummings; Daniel D. Ryan; Bradford R. L. Price

[57] ABSTRACT

A single needle batch-type blood fractionation system for separating plasma from whole blood includes a disposable flow system having a single-lumen phlebotomy needle and associated donor conduit, a flow-through plasma separation filter, and an in-process fluid reservoir. During an initial draw cycle whole blood is pumped through the filter to the in-process reservoir by a peristaltic-type inlet pump operating at a predetermined draw rate. When a predetermined volume of filtered plasma-deficient blood has been collected in the reservoir, as sensed by the weight of the reservoir, the system reverts to a return cycle wherein a portion of the plasma-deficient blood in the reservoir is pumped back to the donor conduit by a peristaltic-type return pump operating at a predetermined return rate higher than the draw rate of the inlet pump. Depending on the relative operating speeds of the inlet and return pumps, an operator-controllable portion of the plasma-deficient blood from the in-process reservoir is returned to the donor through the phlebotomy needle, and the remaining portion is recirculated through the filter. The partial recirculation of plasma-deficient blood through the filter during the return mode reduces the processing time of the system, provides for improved accommodation of whole blood of unusually high or low hematocrit, and enables the use of a smaller and less expensive filter.

14 Claims, 15 Drawing Figures

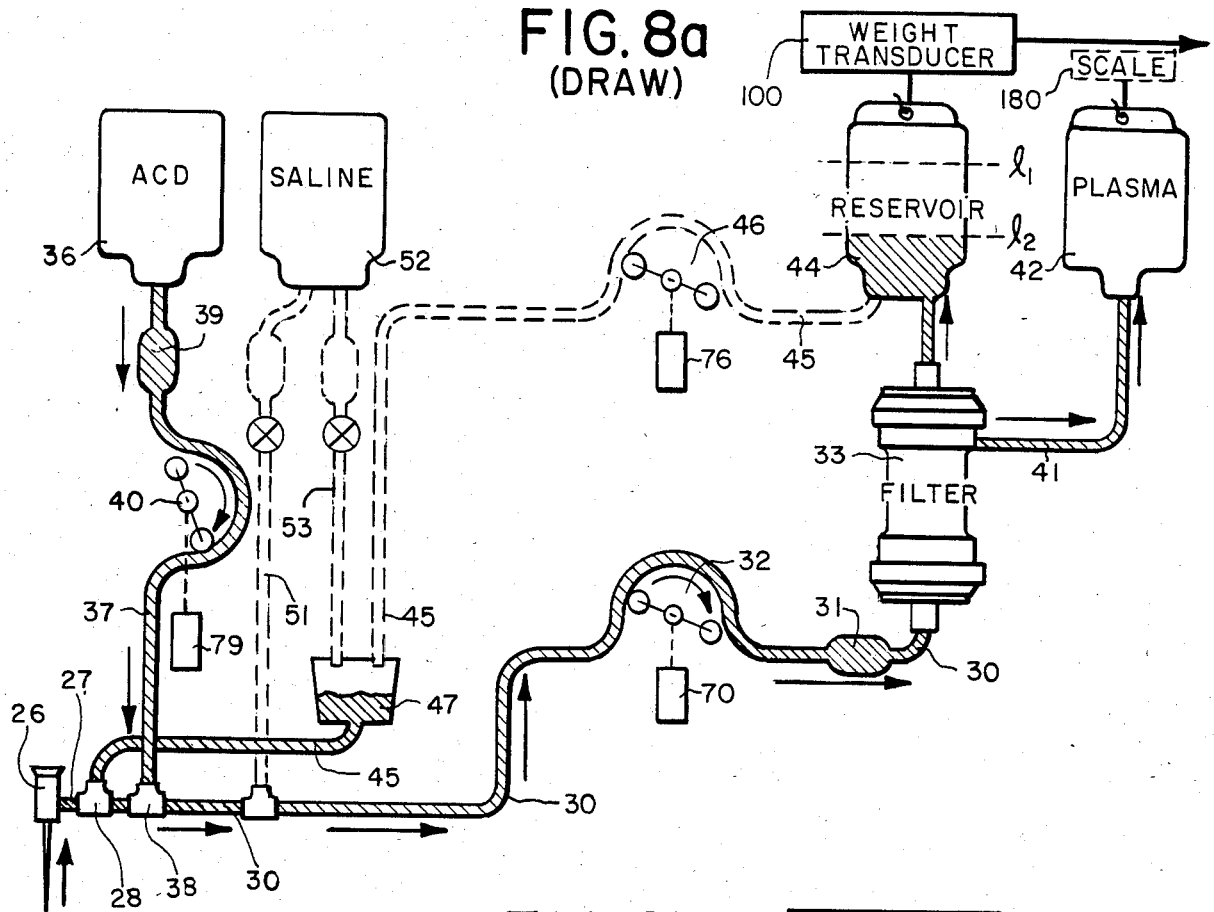
FIG. 8a (DRAW)
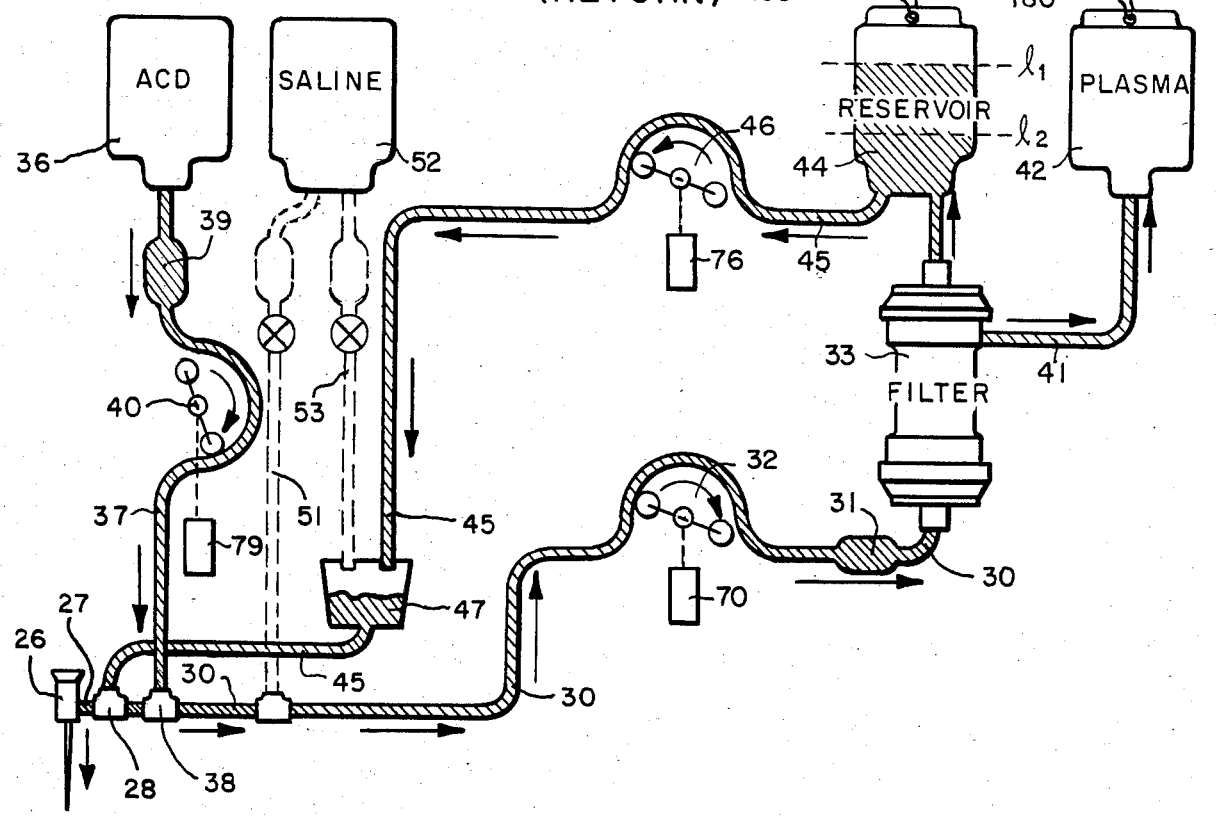
FIG. 8b (RETURN)

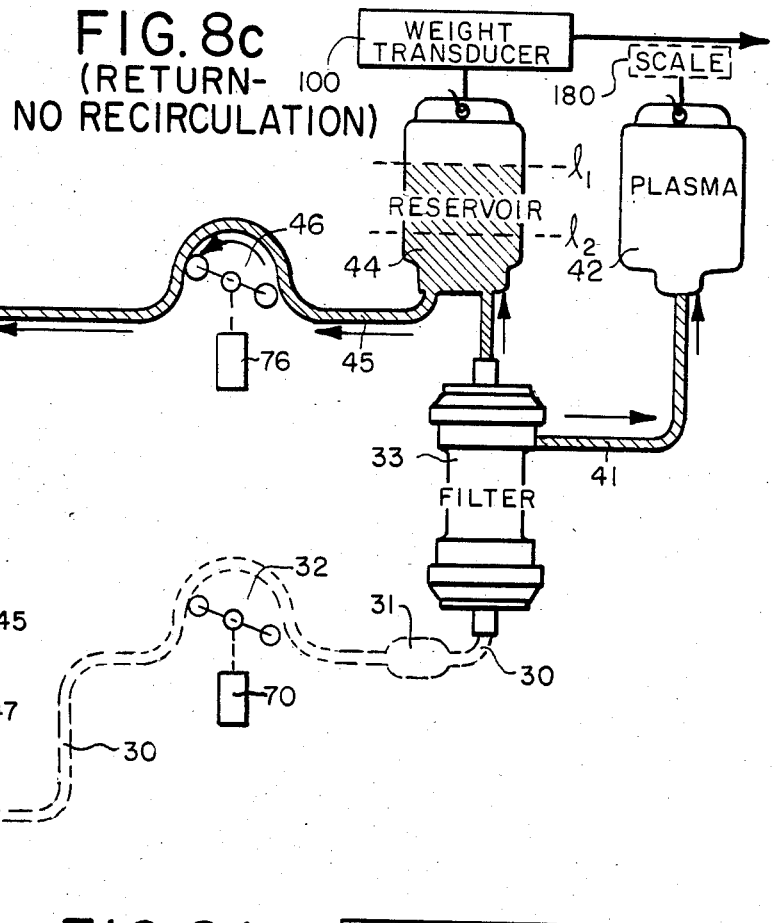
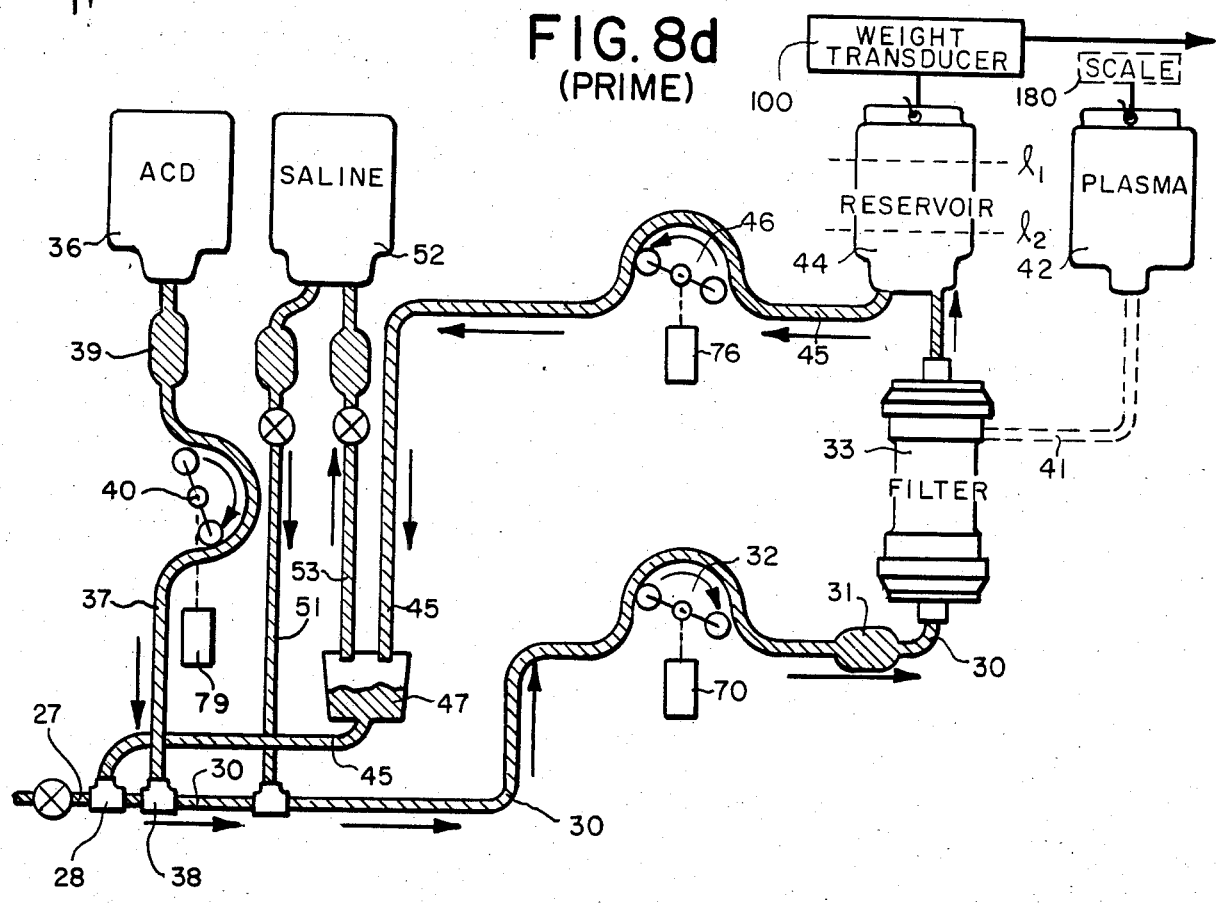
FIG. 8c (RETURN—NO RECIRCULATION)
FIG. 8d (PRIME)

SINGLE NEEDLE BLOOD FRACTIONATION SYSTEM HAVING ADJUSTABLE RECIRCULATION THROUGH FILTER

BACKGROUND OF THE INVENTION

The present invention relates generally to systems and apparatus for processing whole blood, and more specifically to blood fractionation systems and apparatus having a filter component for separating and collecting a desired blood component, such as plasma, from whole blood through a single-lumen phlebotomy needle.

Various methods and apparatus have been developed for the in vivo processing of whole blood, wherein whole blood is taken from a donor, a desired blood component is separated and collected, and the processed blood is returned to the donor. Blood components typically collected using such processing include plasma (plasmapheresis), white blood cells (leukopheresis) and platelets (plateletpheresis).

In vivo blood processing apparatus may be of the centrifugal type, wherein the differing density of the collected blood component causes the component to congregate for collection at a particular radial distance in a centrifuge, or may be of the filter type, wherein the particle size of the collected component allows only that component to pass through a filter membrane into a collection chamber. Filter type apparatus is generally preferable for in vivo plasmapheresis applications, since such apparatus does not require complex rotating machinery and is more compact and less costly to manufacture.

One form of filter which is particularly attractive for use in plasmapheresis apparatus utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collection chamber from which the component is transported to a collection container. A preferred construction and method of manufacture of such a flow-through hollow fiber filter is shown in the copending application of Robert Lee and William J. Schnell, entitled, "Microporous Hollow Fiber Membrane Assembly and Its Method of Manufacture", Ser. No. 278,913, filed June 29, 1981 now abandoned, continuation application Ser. No. 604,396 filed Apr. 26, 1984.

The efficiency of a flow-through filter in separating plasma from whole blood depends on the hematocrit of the donor, and the flow rate and pressure of the whole blood as it is pumped through the filter. Insufficient flow rates or whole blood pressures result in less than optimum yields. Excessive flow rates or whole blood pressures result in hemolysis, or damage to the red blood cells, within the filter, and possible failure of the filter to exclude red blood cells from the collected plasma. Thus, a practical limit exists for the percentage of plasma that can be recovered by a flow-through membrane filter in a single pass of whole blood.

To improve the efficiency of blood fractionation systems it has been proposed that once-filtered plasma-deficient whole blood be recirculated through the filter. This enables the filter to refilter the previously-filtered whole blood, recovering an additional percentage of the remaining plasma component. A blood fractionation system providing such recirculation is described in the copending application of Arnold C. Bilstad et al, entitled, "Increased Yield Blood Component Collection System and Methods", Ser. No. 411,057, filed Aug. 24, 1982 now abandoned, continuation application Ser. No. 690,399 filed Jan. 9, 1985.

However, in certain procedures, as where a high hematocrit is encountered in the whole blood drawn from a donor, the hematocrit of the once-filtered plasma-deficient whole blood may be so high as to require a reduction in the filter flow rate and pressure with an attendant reduction in filter efficiency, to avoid hemolysis in the second pass through the filter. This has the effect of increasing the time required to separate a given quantity of plasma, thereby increasing the inconvenience of the procedure to the donor. Accordingly, the need has developed for a blood fractionation system wherein recirculation through the filter is obtained while maintaining hematocrit, flow rate and pressure parameters which provide optimum system efficiency.

Furthermore, for user comfort it is desirable that in vivo blood fractionation systems withdraw and return whole blood to the donor through a single phlebotomy needle at a single injection site. This necessitates either the use of a single duallumen phlebotomy needle, in conjunction with a continuous flow non-batch system, such as described in the copending application of Arnold C. Bilstad et al, entitled "Blood Fractionation Apparatus", Ser. No. 330,898, filed Dec. 15, 1981, now U.S. Pat. No. 4,447,191, or of a single-lumen phlebotomy needle in conjunction with a bidirectional batch system, whereby batches of whole blood are alternately drawn through the needle, passed through a plasma separation filter, and returned through the same needle. Such bidirectional single-lumen batch systems have the advantage of utilizing a smaller and potentially less traumatic single lumen needle. However, since such systems have heretofore not provided plasma separation from the batch in process during both the draw and return cycles, they have undesirably prolonged the time required to collect a desired volume of plasma.

The present invention is directed to a bidirectional single-needle batch type blood fractionation system which provides for user-controlled partial recirculation of plasma-deficient whole blood through the system filter during the blood return cycle, thereby enabling optimum plasma separation efficiency to be maintained in the system notwithstanding variations in whole blood hematocrit. Basically, whole blood is drawn from the donor through a single phlebotomy needle and associated bidirectional donor conduit and pumped through the filter to a reservoir by an inlet pump. As the whole blood passes through the filter plasma is separated and stored in a separate collection container. Upon reaching a predetermined volume, filtered plasma-deficient whole blood in the reservoir is pumped from the reservoir to the donor conduit by a return pump, which operates at a higher rate than the inlet pump. By reason of the higher rate of the return pump flow is reversed in the donor conduit and a portion of the plasma-deficient whole blood is returned to the donor through the phlebotomy needle, and the remaining portion is recirculated through the filter, without the need for valves for controlling fluid flow in the system. By controlling the relative speeds of the inlet and return pumps, the portion of the plasma-deficient whole blood from the reservoir recirculated through the filter can be varied to maintain a desired hematocrit at the filter.

The present invention, by increasing the plasma separation efficiency of the system, makes a reduction in the volume of the system filter possible. This is advantageous in that it reduces the quantity of extracorporeal blood in process, and the cost of the system filter and the microporous filter material utilized therein.

Accordingly, it is a general object of the present invention to provide a new and improved fluid fractionation system for separating a fluid fraction from whole fluid.

It is a more specific object of the present invention to provide a new and improved blood fractionation system for separating plasma from whole blood.

It is a further object of the present invention to provide filter-type blood fractionation system having reduced in-process volume.

It is a further object of the present invention to provide a filter-type blood fractionation system having improved plasma separation efficiency.

It is a further object of the present invention to provide a new and improved filter-type blood fractionation system having user-controllable recirculation through the filter.

It is a further object of the present invention to provide a new and improved blood fractionation system utilizing a single lumen needle.

It is a further object of the present invention to provide a valveless single-lumen needle blood fractionation system.

SUMMARY OF THE INVENTION

Accordingly, the invention is directed to a single needle blood fractionation system and apparatus for separating plasma from whole blood. In one form the system includes a disposable flow system comprising a phlebotomy needle and an associated bidirectional donor interface conduit, flow-through separation means for separating plasma from whole blood, and an intermediate storage reservoir. An inlet pump is provided to pump whole blood from the donor interface conduit through the filter to the intermediate storage reservoir. A return pump operable at a rate greater than the rate of the inlet pump urges plasma-deficient whole blood from the reservoir to the donor interface conduit. System control means responsive to the volume of whole blood in the intermediate storage reservoir initiate operation of the return pump upon the whole blood in the reservoir reaching a predetermined maximum volume and terminate operation of the return pump upon the whole blood in the reservoir reaching a predetermined minimum volume. By reason of the rate of the return pump being greater than the rate of the inlet pump, upon operation of the return pump a portion of the plasma-deficient whole blood from the reservoir dependent on the ratio of the pump rates is caused to recirculate through the inlet pump to separation means, and the remaining portion of the plasma-deficient whole blood is caused to flow through the donor interface conduit to the donor.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 8a is a simplified flow diagram of the blood fractionation system showing the system in the draw portion of its operating cycle.

FIG. 8b is a flow diagram similar to FIG. 8a showing the blood fractionation system adapted for recirculation in the return portion of its operating cycle.

FIG. 8c is a flow diagram similar to FIG. 8a showing the blood fractionation system adapted for non-recirculation in the return portion of its operating cycle.

FIG. 8d is a flow diagram similar to FIG. 8a showing the plasmapheresis system in its prime mode.

DESCRIPTION OF THE PREFERRED EMBODIMENT

Figure 1:
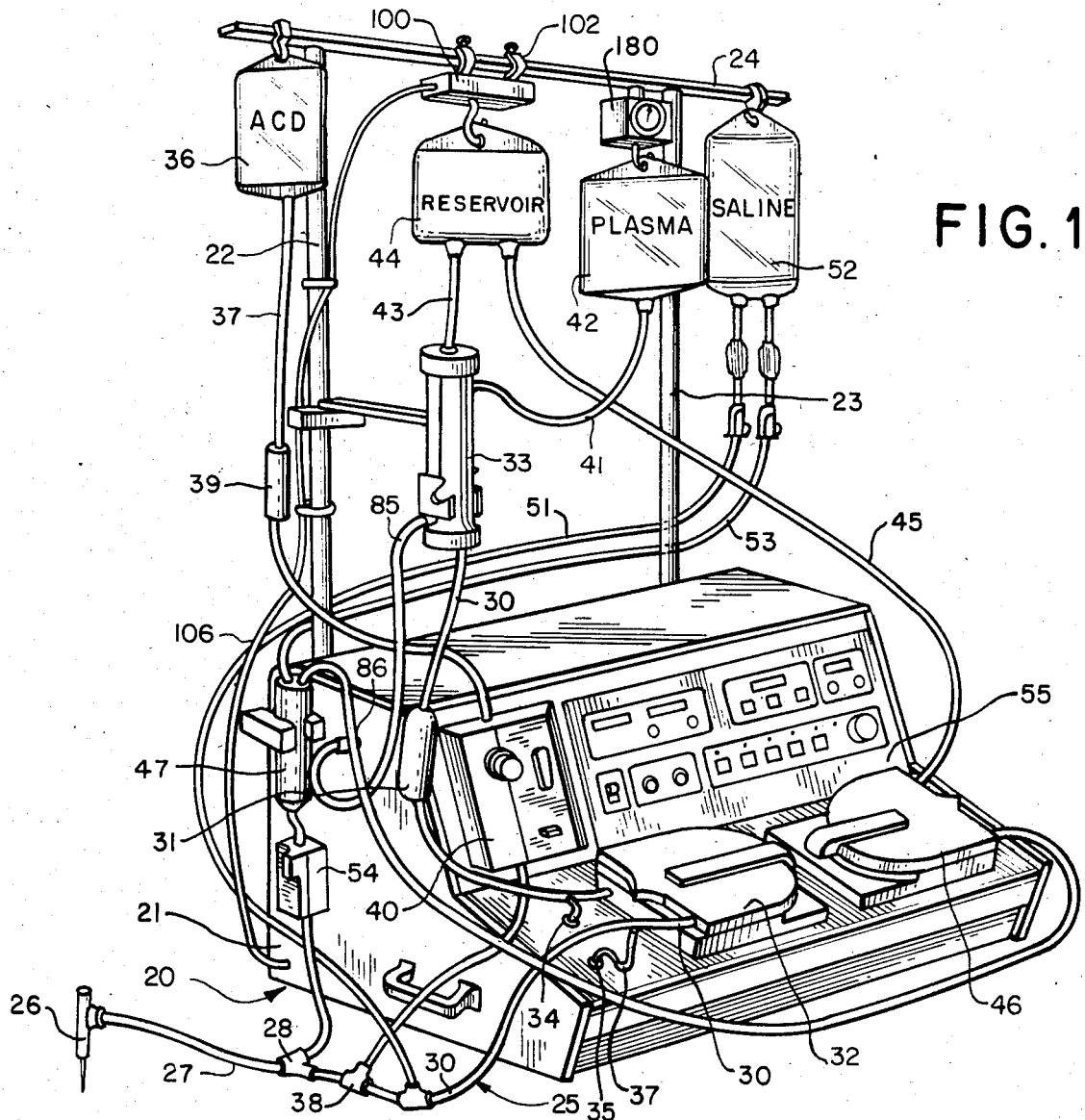
FIG. 1 is a perspective view of a single-needle partial-recirculation plasmapheresis blood fractionation system constructed in accordance with the invention.

Referring to the Figures, and particularly to FIG. 1, a blood fractionation apparatus 20 for use in conjunction with a single-needle filter-type blood fractionation system having filter recirculation in accordance with the invention is seen incorporated within a table-mounted housing 21. The housing preferably includes a pair of vertical support poles 22 and 23 from which a horizontal bar 24 is mounted to allow a plurality of collection and dispensing containers of conventional construction to be hung by means of appropriate hangers.

Figure 2:
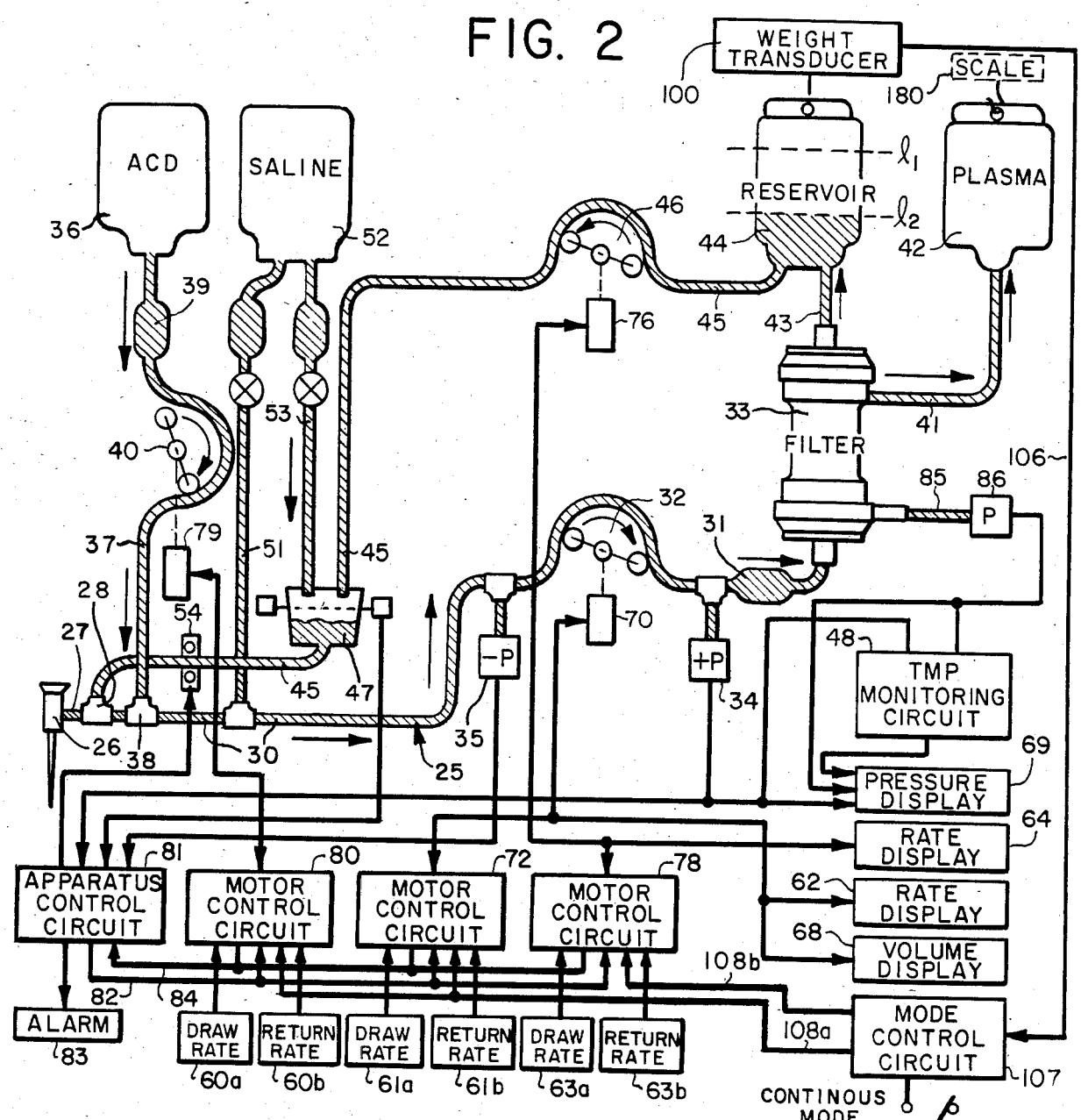
FIG. 2 is a functional block diagram showing the principal components of the blood fractionation system of FIG. 1.

The fractionation apparatus 20 operates in conjunction with a disposable fluid circuit, generally identified by the reference numeral 25 in FIG. 1 and shown schematically in FIG. 2. The fluid circuit 25 includes a plurality of flexible plastic tubing segments which form fluid conduits between various components of the fluid circuit. As shown in FIG. 2, whole blood derived from or returned to a donor is conveyed through the lumen of a single single-lumen phlebotomy needle 26 and a bidirectional donor interface conduit segment 27 to which the needle is connected. Conduit 27 communicates with a T-connector 28, which communicates with a tubing segment 30. Whole blood is conveyed through tubing segment 30 and an inline mixing chamber 31 by a peristaltic-type inlet pump 32 to a hollow fiber-type flow-through filter 33. The operation of the inlet pump is monitored by a positive pressure (+P) monitor circuit 34 connected to tubing segment 30 by a short tubing segment. Negative pressure, such as might occur upon the collapse of a vein, is monitored by means of a negative pressure (−P) monitor circuit 35 connected to tubing segment 30 upline of inlet pump 32 by another short tubing segment.

To prevent blood from clotting while in process anticoagulant (ACD) solution from a supply container 36 is introduced into conduit segment 30 through a tubing segment 37 and a T-connector 38. A drip chamber 39 may be provided inline in segment 38 to monitor ACD flow. A peristaltic-type pump 40 is provided along tubing segment 37 to provide a controlled rate of addition of the anticoagulant fluid to the whole blood.

Plasma separated from whole blood within filter 33 is conveyed by a tubing segment 41 to a plasma collection container 42. The pressure provided by inlet pump 32 provides flow through filter 33 to the collection container. A weight scale of conventional construction may be provided to provide an indication to the user of the volume of plasma collected.

Plasma-deficient blood from filter 33 is conveyed through a tubing segment 43 to an in-process fluid storage reservoir 44. In accordance with the invention, this plasma-deficient blood is periodically withdrawn from reservoir 44 through a tubing segment 45 by a peristaltic-type return pump 46 for return to conduit 27 at T-connector 28. The whole blood conveyed through tubing segment 45 passes through a combined bubble trap and fluid absence detector 47, which may be similar in structure and operation to that described in U.S. Pat. No. 4,341,116 to Arnold C. Bilstad et al.

Reservoir 44 and plasma container 42 are preferably hung at the same height to avoid the need for an equalizer valve at the whole blood and collected plasma outlets of filter 33. However, under other circumstances an equalizer valve may be provided to restrict the plasma outlet port until the pressure of the plasma in the filter reaches that of plasma-deficient blood flowing from the filter, and thereafter to modulate plasma flow through line 41 to maintain the pressure equivalence. A preferred construction for such an equalizer valve is described in the copending applications of Clinton Kopp et al; "Membrane Plasmapheresis Apparatus and Procedure", Ser. No. 277,428 now abandoned, continuation application Ser. No. 542,565 filed Oct. 19, 1983; "Fluid Flow Control Device", Ser. No. 277,449, now U.S. Pat. No. 4,412,553; and "Fluid Flow Control Device", Ser. No. 277,414; filed June 25, 1981 and assigned to the present assignee now U.S. Pat. No. 4,431,019. A transmembrane pressure (TMP) monitoring system 48, which may be as described in the copending application of Arnold C. Bilstad et al, "Trans-Membrane Pressure Monitoring System", Ser. No. 403,362, filed July 30, 1982, now U.S. Pat. No. 4,493,693 may be provided in apparatus 20 to assist the user in making adjustments for maximum operating efficiency of filter 33.

For system priming purposes, a saline fluid may be added to segment 30 through a tubing segment 51, which is connected at one end to a saline container 52 and at its other end to a T-connector in conduit segment 30. A second saline line 53 is provided between container 52 and bubble trap 47 for use in the purging procedure to enable trapped air to escape. Drip chambers and clamps of conventional construction may be provided in lines 51 and 53 to assist the procedure. A safety clamp 54 positioned along tubing segment 45 downline of bubble trap 47 actuates in the event of detection of a bubble or in the event of a malfunction in the apparatus to preclude uncontrolled infusion of fluid into the donor.

Figure 3:
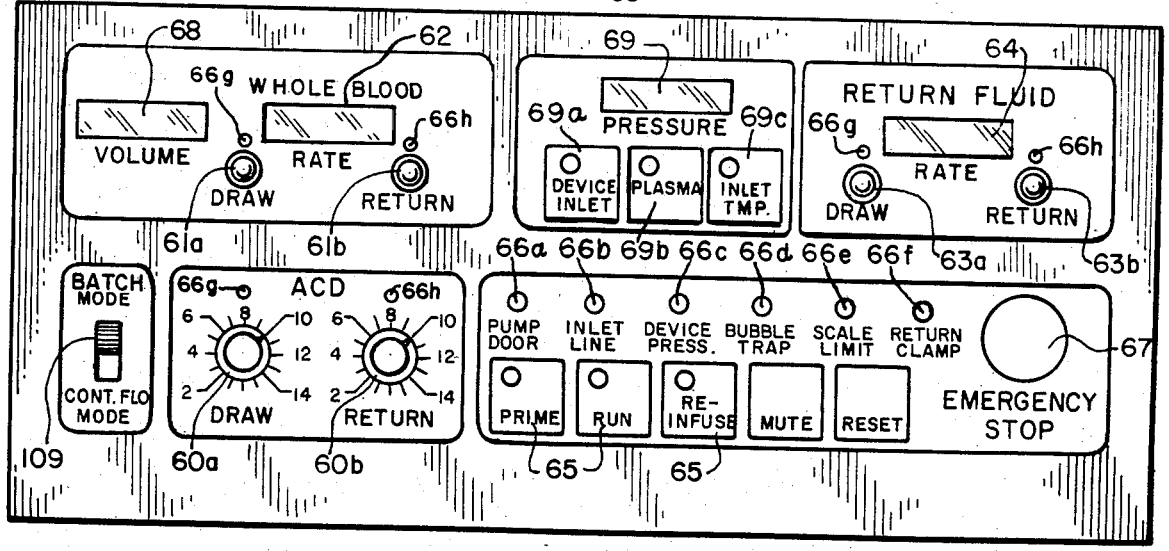
FIG. 3 is an enlarged front elevational view of the control panel of the blood fractionation apparatus of FIG. 1.

Referring to FIG. 1, the blood fractionation apparatus 20 includes a sloped control panel 55 containing operator-actuated controls for operating the apparatus. As shown in FIG. 3, control panel 55 includes a pair of selector switches 60a and 60b by which the draw and return mode operating speeds of anticoagulant pump 40 are set, a pair of potentiometer controls 61a and 61b and a digital readout 62 by which the draw and return mode operating speeds of the inlet pump 32 are controlled, and a pair of potentiometer controls 63a and 63b and a digital readout 64 by which the draw and return mode operating speeds of the return pump 46 are controlled. A plurality of push button switches 65 are provided to establish the operating mode of the apparatus. A plurality of status indicating lights 66a–66f provide status and alarm indications, and three pairs of indicator lights 66g and 66h associated with respective ones of the system pumps indicate the draw and return operating cycles of the pumps. An emergency stop switch 67 provides for an immediate operator-initiated shutdown in the event of a malfunction.

A display 68 displays the total volume of whole blood processed by the apparatus since the beginning of a particular procedure. A display 69 displays fluid pressure readings, as called for by a trio of pushbutton switches 69a–69c. Actuation of switch 69a causes the inlet pressure of filter 33 to be displayed. Actuation of switch 69b causes the collected plasma pressure of the filter to be displayed. Actuation of switch 69c causes the inlet transmembrane pressure (TMP) of the filter to be displayed as derived by TMP monitoring circuit 48.

Referring to FIG. 2, the inlet pump 32 is driven by a motor 70. Power for operating motor 70 is provided by a motor control circuit 72 which responds to potentiometer controls 61a and 61b and a tachometer feedback signal from a tachometer (not shown in FIG. 2) associated with the motor to maintain a desired motor operating speed. The inlet pump flow rate is displayed by readout 62 as part of a display circuit which responds to the tachometer output signal.

Similarly, the return pump 46 is driven by a motor 76. Power for motor 76 is provided by a motor control circuit 78 which responds to a tachometer feedback signal from a tachometer (not shown in FIG. 2) associated with the motor and panel-mounted potentiometers 63a and 63b to maintain a desired constant motor speed. The return pump flow rate is displayed by readout 64 as part of the display circuit.

The anticoagulant pump 40 is driven by a stepper motor 79. Drive signals for motor 79 are developed by a motor control circuit 80 which responds to rate selection switches 60a and 60b to maintain a desired anticoagulant flow rate.

The operation of the various pump motors is controlled by a control circuit 81 which includes the mode select pushbutton switches 65 on control panel 55. Certain system conditions, such as negative pressure at pressure monitor 35, or excessive positive pressure at pressure monitor 34, or the occurrence of a bubble or other fluid absence as signaled at the output of the combined bubble trap and fluid absence detector 47, result in the application of an alarm signal to control circuit 81. This circuit in turn produces a control signal which is applied to motor control circuits 72, 78 and 80 by way of a motor control line 82 to interrupt operation of the motors. In addition, an alarm 83 associated with the control circuit may be sounded and an appropriate one of indicator lamps 66a–66f may be lit to alert the operator. Each of motor control circuits 72, 78 and 80 also includes internal stall protection whereby an alarm signal is developed and applied to control circuit 81 by way of a control line 84 to terminate operation of blood fractionation apparatus 20 in the event of a pump malfunction.

Basically, the hollow fiber membrane-type filter device 33 employed in blood fractionation apparatus 20 includes a generally cylindrical housing within which a bundle of microporous hollow fibers are mounted. The housing includes end caps which close the ends of the housing to form a plasma collection chamber within the housing. A whole blood inlet port is formed on one end cap, and a whole blood outlet port is formed on the other end cap. Blood introduced through the inlet port enters the adjoining open ends of the hollow fiber membrane elements and proceeds to flow lengthwise through the fibers. Plasma in the whole blood flows through the micropores in the hollow fibers and out into the collection chamber formed within the housing circumferentially surrounding the bundle. The housing includes two side plasma outlet ports which communicate with the collection chamber. One outlet port communicates with the plasma collection container 42 to collect plasma separated by the filter. The other outlet port is used to sense plasma outlet pressure in conjunction with a tubing segment 85, a pressure transducer 86, and the transmembrane pressure (TMP) monitoring system 48. Plasma-deficient blood (containing red cells, leukocytes and platelets), having passed through the hollow fiber membrane elements, exists through the outlet port for temporary storage in the intermediate in-process fluid reservoir 44.

In accordance with the invention, plasma-deficient whole blood in reservoir 44 is periodically pumped by return pump 46 back to donor conduit segment 27. Inlet pump 32 continues to operate at this time at a rate set by the operator, so that a portion of the returned plasma-deficient blood dependent on the ratio of the return pump rate to the whole pump rate is recirculated through filter 33, thereby continuing plasma collection during the return cycle. For example, with inlet pump 32 continuously operating at 60 ml./min., and return pump 46 operating at 100 ml./min., 60 ml./min., or 60% of the processed plasma-deficient blood, is recirculated through the filter, and 40 ml./min, or 40%, is returned to the donor.

In performing a normal batch-mode procedure blood fractionation apparatus 20 operates in alternate draw and return cycles. During each draw cycle inlet pump 32 operates to draw whole blood through the phlebotomy needle into conduit 27 and to advance the whole blood through tubing 30 and mixing chamber 31 to filter 33. After a predetermined volume of plasma-deficient whole blood has been pumped through filter 33 into reservoir 44, the draw cycle is terminated and the return cycle is initiated. Return pump 46 then operates to pump plasma-deficient blood from reservoir 44 into conduit 30 at T-fitting 28. Depending on the relative operating speed of return pump 46 and inlet pump 32, a user-selectable portion of the plasma-deficient whole blood is pumped into mixing chamber 31 for subsequent recirculation through filter 33, and the remaining portion is returned to the donor through donor tubing segment 27 and needle 26. Upon the volume of the plasma-deficient blood in reservoir 44 reaching a predetermined minimum level, the return cycle is terminated and the draw cycle is again initiated. The cycles continue in alternation until a desired quantity of blood has been processed or a desired quantity of plasma has been collected.

Figure 4:
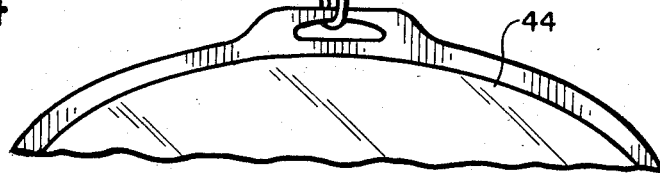
FIG. 4 is an enlarged front elevational view partially in section showing the electrical weight transducer of the system in conjunction with the in-process fluid reservoir of the system.

The blood fractionation apparatus 20 is, in further accord with the invention, conditioned between the draw cycle and the return cycle by a circuit responsive to the weight of the intermediate in-process fluid reservoir 44. To this end, the blood fractionation apparatus 20 includes a weight transducer unit 100 from which the reservoir container 44 is suspended. As shown in FIG. 4, the weight transducer unit 100 may include a housing 101 mounted by clamps 102 or other appropriate means to the horizontal support bar 24 of the apparatus. Within housing 101 reservoir 44 is suspended from the sense pin 103 of an electrical weight transducer 103, which may be conventional in construction and operation, provides an electrical output signal which is conveyed to the apparatus housing 21 through a connecting cable 106.

Within housing 21, blood fractionation apparatus 20 includes a mode control circuit 107 (FIG. 2) which provides, in accordance with the magnitude of the signal from weight transducer 100, a pair of mode control signals from application to motor control circuits 72, 78 and 80 by way of a control line 108a and 108b. A mode select switch 109, located on control panel 55 (FIG. 3), is provided to enable the user to selectively disable mode control circuit 107 when it is desired to operate the plasmapheresis apparatus as a continuously running system, as in conjunction with a continuous-flow two needle in vivo blood fractionation procedure.

Figure 5:
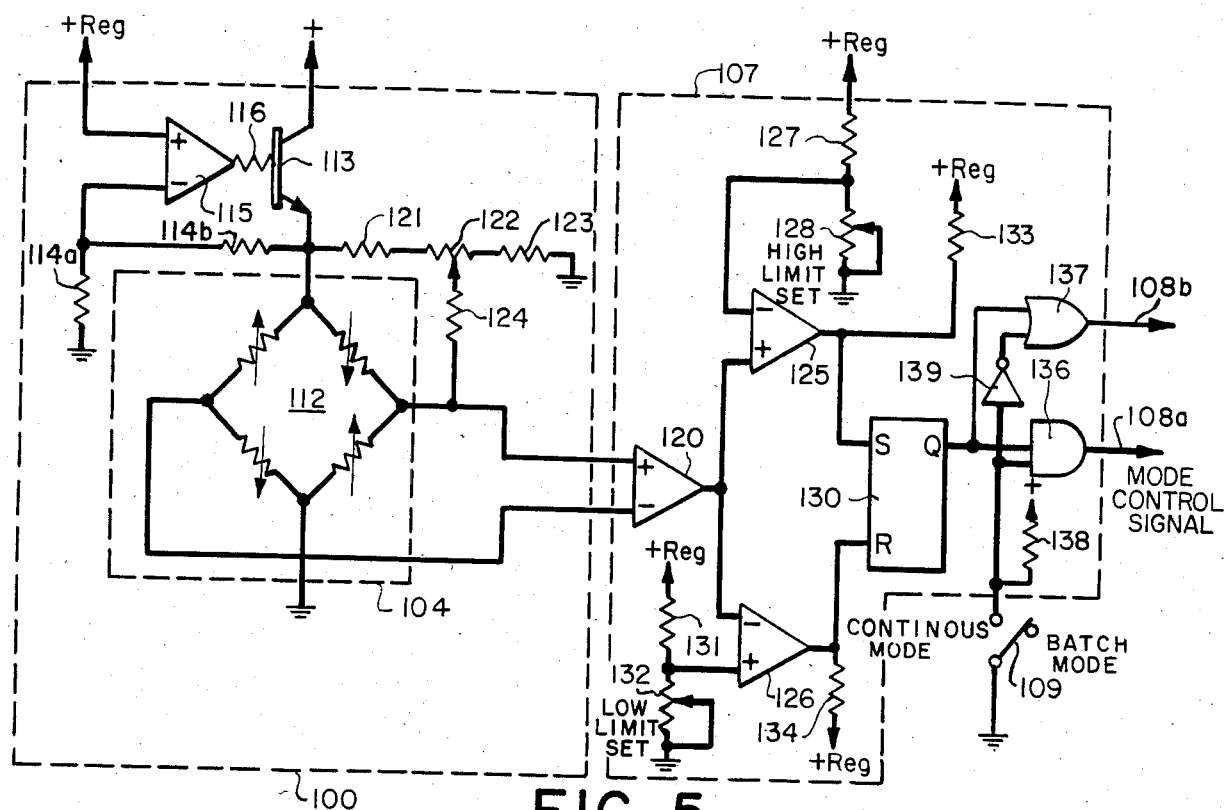
FIG. 5 is a simplified schematic diagram of the mode control circuit of the blood fractionation system.

Referring to FIG. 5, within the weight transducer unit 100 the weight transducer 104 is seen to comprise a strain gauge bridge circuit 112. One input terminal of network 112 is connected to a source of positive current through a series-connected transistor 113, and the other input terminal is connected to ground. The conduction level of transistor 113, and hence the voltage applied to network 112, is controlled by a differential amplifier 115 having its non-inverting input connected to a source of regulated voltage, and its inverting input connected to a voltage divider comprising resistors 114a and 114b. The output of differential amplifier 115 is connected to the base of transistor 113 through a resistor 116, with the result that the voltage applied to network 112 is held constant at all times.

The output of bridge circuit 112, which depends on the force exerted on sense pin 103, is applied to a differential amplifier 120 included in mode control circuit 107. A necessary offset is introduced to this signal by an adjustable voltage divider network comprising resistors 121, 122, 123 and 124 connected between the regulated input terminal of network 112 and ground and the non-inverting input of differential amplifier 120.

To establish predetermined minimum and maximum volume thresholds for the plasma-deficient whole blood in reservoir 44 the output of differential amplifier 120 is applied to the non-inverting input of a comparator amplifier 125 and to the inverting input of a comparator 126. The inverting input of amplifier 125 is connected to a voltage divider comprising a resistor 127 and a potentiometer 128 connected between a source of regulated voltage and ground, and the inverting input. Depending on the setting of potentiometer 128, comparator amplifier 125 produces a logic high output signal as the volume of whole blood reaches a predetermined maximum level within reservoir 44. This output signal is applied to the set input of an RS-type flip-flop 130 which provides at its Q output the draw and return cycle mode control signal.

The non-inverting input of comparator amplifier 126 receives a reference voltage developed by a voltage divider comprising a resistor 131 and a potentiometer 132. Depending on the setting of potentiometer 132, the threshold of comparator amplifier 126 is varied to establish the minimum threshold level. Comparator 126 produces a logic low output which is applied to the reset input of flip-flop 130. Resistors 133 and 134 supply necessary operating current to the outputs of comparator amplifiers 125 and 126.

To enable blood fractionation apparatus 20 to be used for a continuous flow procedure wherein the ACD, inlet and return pumps are continuously controlled by controls 60a, 61a and 63a, respectively, an AND gate 136 is connected between the Q output of flip-flop 130 and control line 108a, and an OR gate 137 is connected between the Q output and control line 108b. One input of gate 136 is connected to a positive current source by a resistor 138, and to ground by mode switch 109. Gate 129 is similarly connected through an inverter 139. When switch 109 is open, corresponding to operator selection of a continuous-flow procedure, AND gate 136 is inhibited, rendering control line 108a logic low and control line 108b logic high, causing the pumps to operate continuously under the controls of 60a, 61a and 63b. However, when switch 109 is closed, AND gate 136 is enabled and the logic state of control line 109 is dependent on the operating state of RS flip-flop 130, and hence the volume of plasma-deficient blood accumulated in reservoir 44.

Figure 6A:
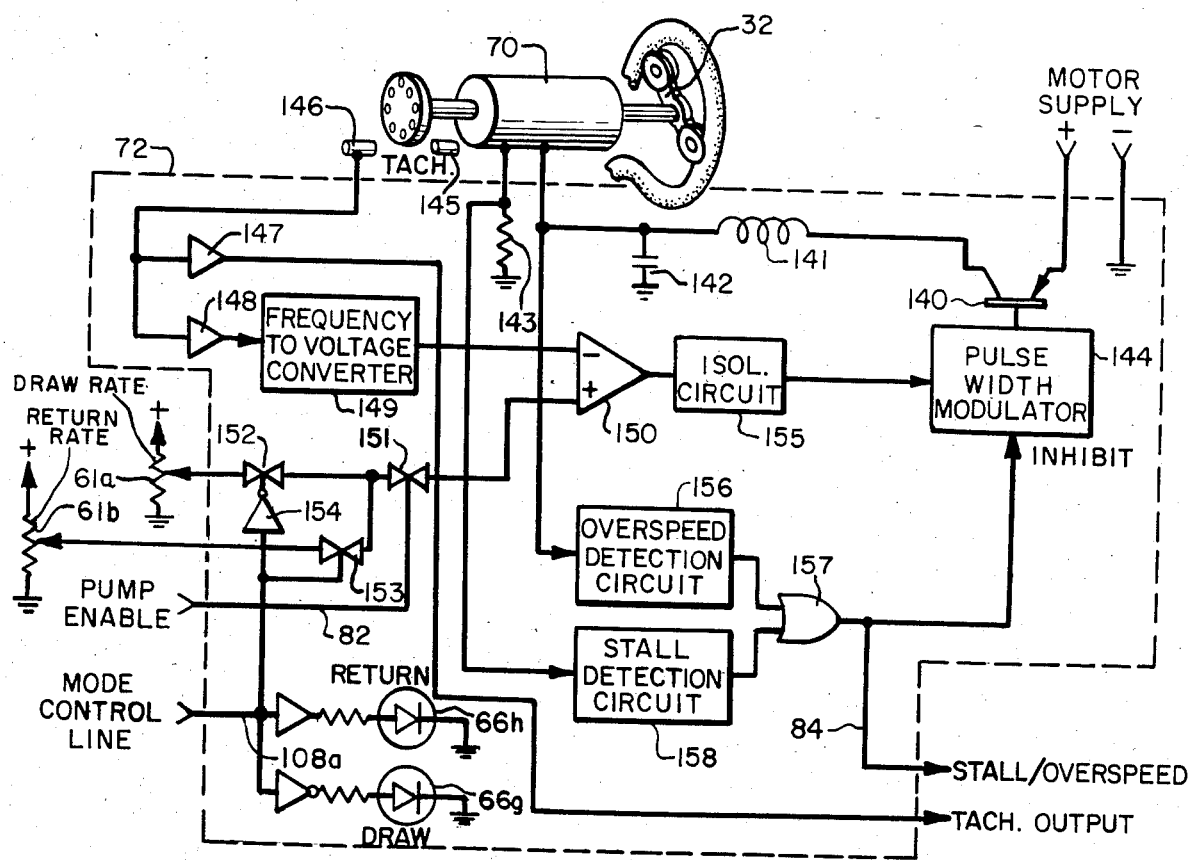
FIG. 6a is a simplified schematic diagram of the inlet pump motor control circuit of the blood fractionation system.

Referring to FIG. 6a, the motor control circuit 72 provided for supplying operating power to the inlet pump motor 70 comprises a series-connected power transistor 140 and a reactance control network comprising an inductance 141 and a capacitor 142. These components supply power from a unidirectional motor current source (not shown) to the motor. The return line from the motor includes a series-connected current metering resistor 143.

Pump motor 70 is a direct current type motor and receives excitation over a variable duty cycle through power transistor 140. Conduction of this transistor is controlled by a pulse width modulator 144 which provides an appropriate control signal to the base electrode of the transistor. A tachometer formed by a light emitting diode 145 and a photodetector 146 operates in a conventional manner to provide output pulses indicative of incremental rotation of the pump motor. These pulses are applied to a tachometer output line through an amplifier 147 for use by other systems within the apparatus, and through an amplifier 148 to a frequency-to-voltage converter circuit 149. This circuit develops an analog output voltage in proportion to the frequency of the tachometer pulses. This signal is applied to the inverting input of a comparator amplifier 150, wherein it is compared with a speed control signal applied to the non-inverting input from potentiometer 61a or 61b through a trio of analog devices 151–153.

The control gate of switch device 151 is connected to the pump control line 82 so that in the absence of an appropriate motor enabling signal from the apparatus control circuit 81 no reference signal is applied to comparator 150. The control gate of switch device 152 is connected to mode control line 108a through an inverter 154 so that in the absence of a logic high signal on this control line an analog control signal may be applied to comparator 150 by the draw mode whole blood rate control potentiometer 61a. The control gate of switch device 153 is connected directly to mode control line 108, so that in the presence of a logic high signal on this line the output of the return rate potentiometer 61b is applied to comparator 150.

Comparator amplifier 150 operates in a conventional manner to produce an output signal indicative of the difference between its inputs. This output signal is applied through an isolation circuit 155 to pulse width modulator 144, wherein it controls the duty cycle of power transistor 140, and hence the speed of pump motor 70.

Figure 6B:
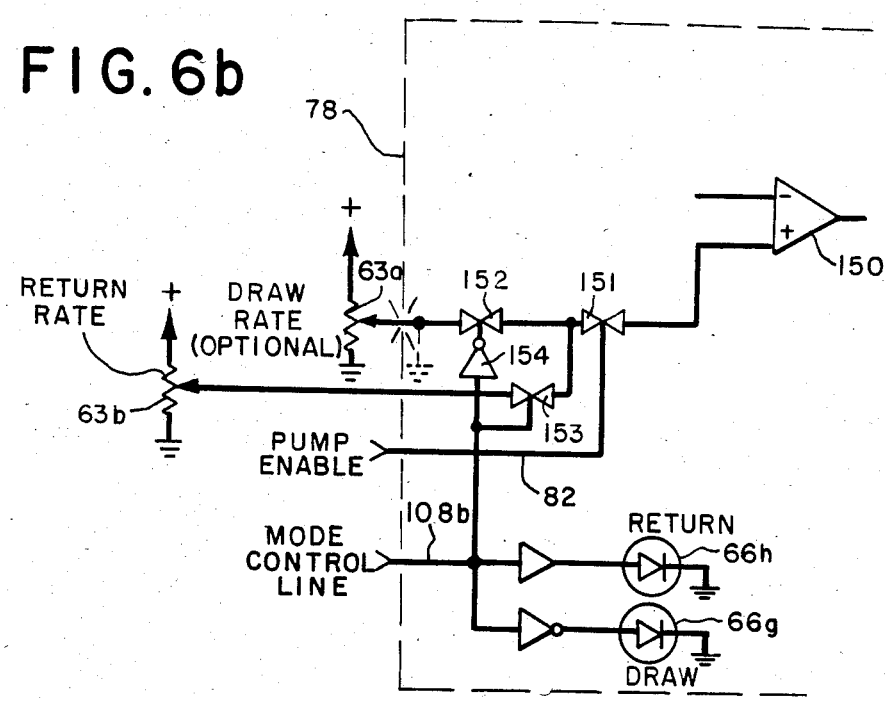
FIG. 6b is a simplified schematic diagram of a portion of the return pump motor control circuit of the blood fractionation system.

Referring to FIG. 6b, the return pump motor control circuit 78 may be identical to motor control circuit 72, except for the input circuit provided for potentiometer rate controls 63a and 63b and control line 108b.

To provide protection against overspeed operation, the excitation level applied to pump motor 70 is continuously monitored by an overspeed detection circuit 156. In the event of an overspeed condition, this circuit provides an output which is coupled through an OR gate 157 to the alarm output line 84, and to the inhibit input of pulse width modulator 144, wherein it prevents the application of current to the base of transistor 140, thereby stopping the motor. Additional protection against malfunction is provided by a stall detection circuit 158 which provides an input to OR gate 156 upon motor 70 becoming stalled, as detected by the voltage level across series-connected resistor 143.

Figure 7:
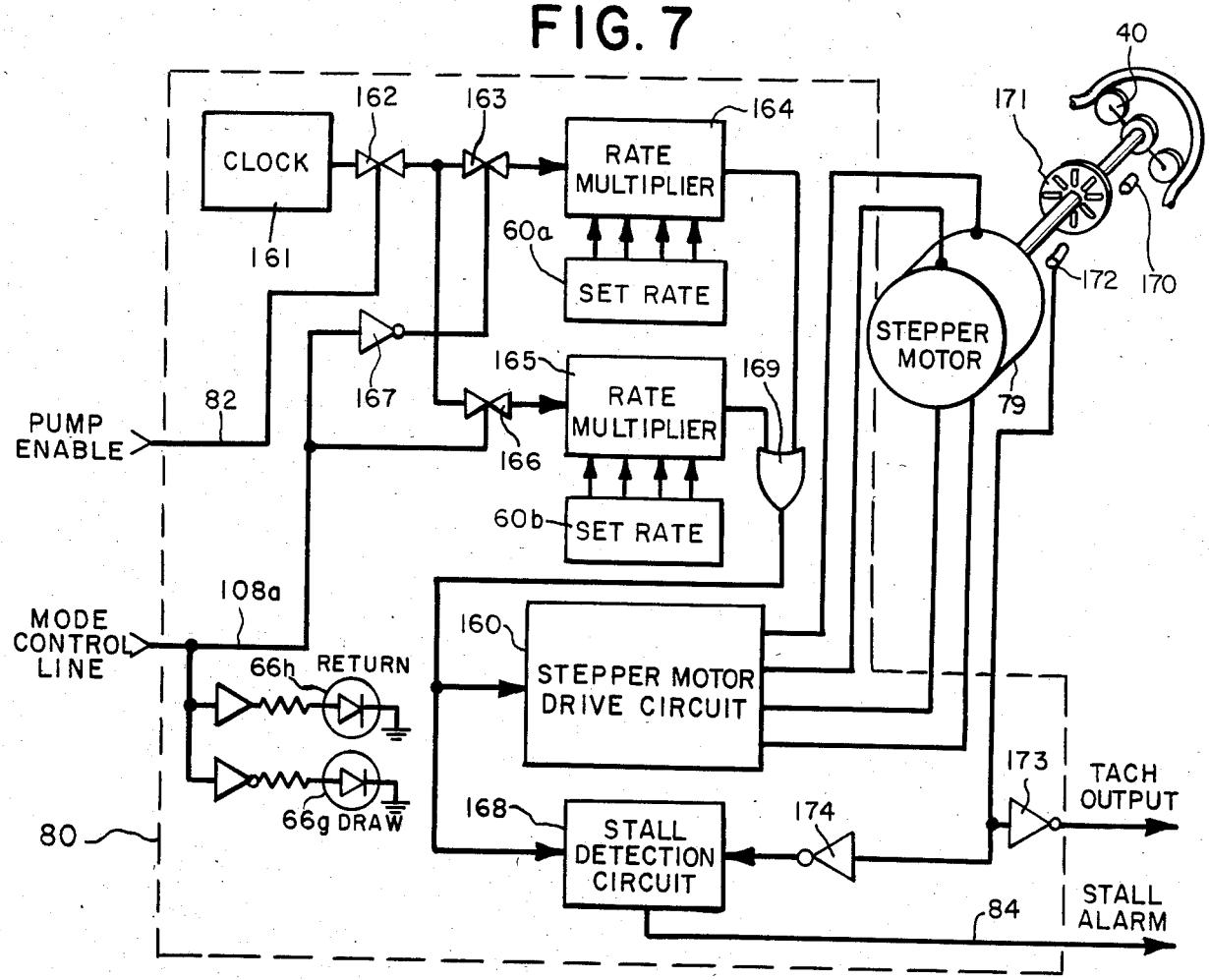
FIG. 7 is a simplified schematic diagram of the ACD pump drive circuit of the blood fractionation system.

Referring to FIG. 7, a multi-phase drive signal is applied to the anticoagulant pump stepper motor 79 by a stepper motor drive circuit 160 of conventional design. Control pulses for initiating the multi-phase drive signal from drive circuit 160, and consequently each incremental rotation of the motor, are provided by a clock circuit 161. In the draw mode, output pulses from the clock are applied through a pair of analog switch devices 162 and 163 to a rate multiplier 164. Rate multiplier 164, which may be conventional in construction and operation, responds to an operator-selected rate set by switch 60a to provide a preselected rate multiplication to the applied clock pulses. This results in stepper motor drive circuit 160 being impulsed at a user-selected rate, and consequently the stepper motor 79 being driven at the desired rate.

Alternatively, clock pulses from clock 161 are supplied to a second rate multiplier 165 through switch device 162 and a third analog switch device 166. When devices 162 and 166 are conductive, rate multiplier 165 is active to control motor speed according to the setting of return mode rate selector switch 60b.

Control over operation of stepper motor 79 is obtained by apparatus control circuit 81 by applying the pump enable control signal developed on control line 82 to analog switch device 162. During batch mode operation of the blood fractionation apparatus, analog switch device 162 is enabled continuously. Switch device 163, which is connected to mode control line 108 through an inverter 167, is enabled during each draw cycle to render switch 60a operative. Switch device 166, which is connected directly to control line 108a, is conductive only during each return cycle. Consequently, switch 60b controls return rate. In a non-recirculation procedure, control line 108a provides a continuous logic low signal and only rate multiplier 164 and switch 60a are utilized. The outputs of rate multipliers 164 and 165 are applied to stepper motor drive circuit 160 and a stall detection circuit 168 through an OR gate 169.

The anticoagulant pump drive circuit 80 also includes a tachometer comprising a light emitting diode 170, a slotted disk 171 and a photodetector 172. As disk 171 turns with motor 79, output pulses produced by photodetector 172 are supplied through a first inverter amplifier 173 to a tach output line. Pulses are also supplied through a second inverter amplifier 174 to stall detector 168, which provides an output on alarm line 84 upon stepper motor 79 stalling.

The operation of blood fractionation system 20 is illustrated in FIGS. 8a–8d and 9. In the batch mode, the system operates as illustrated in FIGS. 8a and 8b. Where no recirculation through the filter is desired in the batch mode, the system operates as illustrated in FIGS. 8a and 8c. Where the system is to be primed, the system operates as illustrated in FIG. 8d.

During the draw cycle, as shown in FIG. 8a, whole blood is drawn from a donor through a single-lumen phlebotomy needle 26 and the bidirectional donor interface conduit 27 by inlet pump 32, which pumps the whole blood along conduit segment 30 to mixing chamber 31. Within the mixing chamber, the freshly drawn whole blood is, in accordance with one aspect of the invention, mixed with whole blood previously advanced along segment 30 by pump 32, and the resulting mixture is advanced through filter 33 to reservoir 44.

As the mixed whole blood from chamber 31 passes through filter 33, a portion of the plasma component contained therein is separated from the whole blood by the membrane element of the filter and is caused to flow through tubing segment 41 to plasma collection container 42. The volume of plasma thus collected can be readily determined by reference to a conventional weight scale 180 from which the plasma collection container is suspended. Alternatively, a collected volume monitoring system such as that described in the copending application of Arnold C. Bilstad et al, entitled "Blood Fractionation Apparatus Having Collected Volume Monitoring System", Ser. No. 330,899, filed Dec. 15, 1981, now U.S. Pat. No. 4,458,539 may be utilized to provide a direct readout of collected plasma volume.

During the draw cycle the operating rate of the inlet pump 32 is set by potentiometer 61a. The operating rate of the return pump 46, which is normally not operative during the draw cycle, may be set to zero by setting potentiometer 63a to zero. As an alternative, to preclude operation of the return pump 46 during the draw cycle, potentiometer 63a may be eliminated in the replacement pump motor control circuit 78 and the input to analog switch device 152 in that circuit may be connected to ground, as shown in FIG. 6b. The operating rate of ACD pump 40 is set by selector switch 60a to operate a rate appropriate to the operating rate of inlet pump 32 to maintain a desired ratio of ACD to whole blood.

The plasma-deficient whole blood from the filter continues to collect in reservoir 44 during the draw cycle. As the weight of the whole blood in the reservoir increases, transducer 100 produces a progressively increasing output signal. When this signal reaches a level corresponding to fluid level $l_1$, in reservoir 44, the signal applied to comparator 125 (FIG. 5) by differential amplifier 120 causes comparator 125 to produce an output signal which conditions RS flip-flop 30 to its set state. As a consequence, the Q output of flip-flop 130 becomes logic high, and, assuming AND gate 136 is enabled by mode switch 109 being open for batch operation, mode control line 108a conveys a logic high control signal. This causes termination of the draw cycle and initiation of the return cycle.

During the return cycle, as illustrated in FIG. 8b, return pump 46 is operated to pump plasma-deficient whole blood from reservoir 44 back through conduit segment 45 to donor conduit 27 and conduit segment 30 at T-connector 28. The flow rate of the plasma-deficient whole blood, as established by return pump 46, under the control of potentiometer 63b, is set higher than the flow rate of the whole blood in conduit segment 30, as established by inlet pump 32 under the control of potentiometer 61b. As a result, the plasma-deficient whole blood flowing from reservoir 44 is caused to divide between donor conduit 27, wherein it causes a flow reversal and flow into the donor through the lumen of the single-lumen phlebotomy needle, and conduit segment 30, wherein it is advanced toward mixing chamber 31 and filter 33.

Within mixing chamber 31 the recirculating portion of the plasma-deficient whole blood divided into conduit segment 30 is caused to mix with whole blood previously pumped into the chamber, as during the previous draw cycle of the system. The resulting mixture, which has a hematocrit determined by the hematocrits of the recirculating plasma-deficient whole blood and the previously pumped resident whole blood, is advanced through filter 33 into reservoir 44 by inlet pump 32. This causes an additional quantity of plasma to be separated from the whole blood mixture by filter 33 and stored in plasma container 42.

The ratio of plasma-deficient whole blood returned to the donor to plasma-deficient whole blood recirculated through filter 33 is dependent on the relative operating rates of the inlet pump 32 and the return pump 46. For a relatively higher return pump rate, a higher percentage of plasma-deficient whole blood is returned to the donor. The actual operating rates of the inlet and return pumps during the return cycle are set by the operator by means of potentiometers 61b and 63b on panel 55. In practice, these rates are limited by practical considerations, such as the flow rate and pressure requirements of filter 33, the maximum permissible draw and return rates of the donor, and the capacity of the conduit segments and associated system components. The ACD pump 40 may be operated during the return cycle at a rate selected by selector switch 60b to maintain a desired percentage of ACD solution in the in-process whole blood.

Operation in the return cycle continues until the volume of plasma-deficient whole blood in fluid reservoir 44 reaches a predetermined minimum level, corresponding to level $l_2$ in FIG. 8b. At this time the output signal produced by weight transducer 100 causes comparator 126 (FIG. 5) to toggle RS flip-flop 130 to its reset state, causing a logic low on mode control lines 108a an 108b.

This causes analog switch devices 152 (FIGS. 6a and 6b) and 163 (FIG. 7) to close and analog switch devices 153 and 166 to open, thereby enabling the inlet pump draw cycle potentiometer 61a (and replacement pump draw cycle potentiometer 63a in a similar manner) and the ACD draw cycle rate selector switch 60a. Consequently, the return cycle is terminated and a new draw cycle is initiated.

Figure 9:
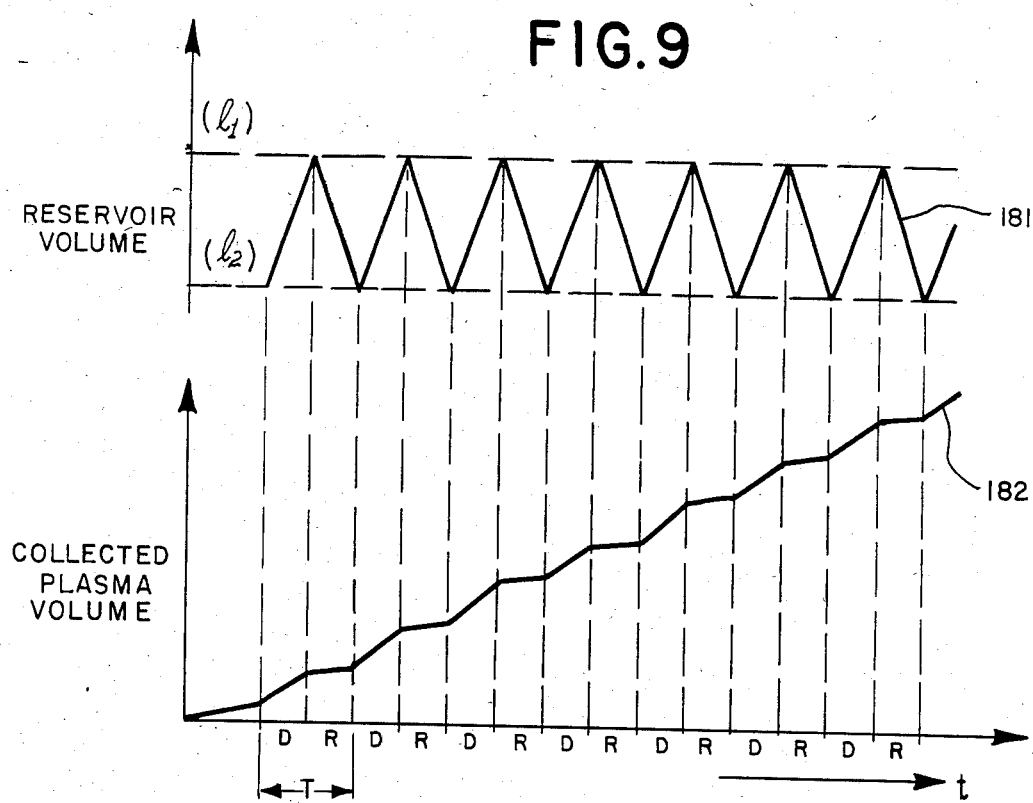
FIG. 9 is a simplified depiction of plasma collection versus time useful in comparing the operation of various types of blood fractionation systems.

Referring to FIG. 9, during alternate draw and return cycles of blood fractionation system 20 the volume 181 of plasmadeficient blood in reservoir 44 is seen to vary between a predetermined maximum level, corresponding to level $1_1$, and a predetermined minimum level, corresponding to level $1_2$. At the same time, the volume 183 of plasma collected in container 42 is seen to increase with each cycle, at a faster rate during draw cycles as freshly drawn blood is filtered, and at a slower rate during return cycles, as recirculated blood is filtered with previously drawn blood. Normally, the fractionation procedure is continued until a desired volume of plasma (or other desired blood fraction) has been collected, as determined by the weight of the collected plasma as read on scale 180.

As a result of the partial recirculation of plasma-deficient whole blood from reservoir 44 during each return cycle, the system filter operates during both draw and return cycles and the time required for separating a given volume of plasma is significantly reduced.

For example, the effect of recirculation through the filter for a system yield of 600 ml. plasma, a donor of 5000 ml. whole blood, a 200 ml./min. return pump rate, a mixing chamber volume of 30 ml., and an in-process fluid reservoir having a predetermined maximum volume of 50 ml. and a predetermined minimum volume of 30 ml., can be summarized for varying whole blood hematocrits and flow rates as follows:

Where it is desired to operate the blood fractionation system without recirculation, as where a donor is encountered having an unusually high hematocrit which raises the probability of hemolysis in a second pass through the filter, the operating speed of the inlet pump during the return cycle can be set to zero by means of potentiometer 61b. Then, as shown in FIG. 8c, all of the plasma deficient whole blood pumped from reservoir 44 during the return cycle is caused to flow back to the donor through the donor interface conduit 27 and the single lumen phlebotomy needle 26. Inlet pump 32, being motionless, functions as a valve to prevent flow through tubing segment 30, thereby obviating the need for separate fluid flow control valves and their attendant control systems.

Where exceptionally low hematocrits are encountered, substantially all of the plasma deficient whole blood from reservoir 44 can be recirculated through filter 33 by setting the inlet pump 32 and the replacement pump 46 to operate at the same rate. It is contemplated that this procedure would be used only for short time periods, such as required to complete a second pass through the filter, to avoid subjecting the filter to excessively high hematocrits and attendant hemolysis.

During the draw and return cycles the ACD pump 40 introduces ACD solution into conduit segment 30 at respective rates selected by the operator. The operation of the ACD pump and the rate selected are options available to the physician and may vary according to the particulars of the procedure.

Prior to initial operation of the blood fractionation system a prime mode may be provided wherein air is removed from the conduit segments and fluid path elements of the system. As shown in FIG. 8d, the saline lines 51 and 53, heretofore clamped closed during the drawn and return cycles, are opened. The donor con-

| Whole Blood Flow Rate (ml/min) | Donor Hematocrit (%) | NO RECIRCULATION | | | WITH RECIRCULATION | | |
|---|---|---|---|---|---|---|---|
| | | Procedure Time (min) | Blood Processed (ml) | Max Filter Hematocrit (%) | Procedure Time (min) | Blood Processed (ml) | Max Filter Hematocrit (%) |
| 50 | 40 | 44.5 | 1690 | 41 | 39.7 | 1520 | 48 |
| 50 | 45 | 48.5 | 1831 | 46 | 42.9 | 1631 | 53 |
| 50 | 50 | 53.2 | 1990 | 51 | 46.7 | 1765 | 58 |
| 50 | 55 | 58.5 | 2178 | 56 | 51.3 | 1923 | 62 |
| 60 | 40 | 39.6 | 1667 | 41 | 34.0 | 1454 | 48 |
| 60 | 45 | 42.9 | 1802 | 46 | 36.6 | 1555 | 54 |
| 60 | 50 | 46.8 | 1958 | 51 | 39.9 | 1686 | 58 |
| 60 | 55 | 51.5 | 2138 | 56 | 43.6 | 1835 | 63 |
| 70 | 40 | 36.5 | 1694 | 41 | 30.5 | 1451 | 51 |
| 70 | 45 | 39.5 | 1826 | 46 | 33.1 | 1556 | 56 |
| 70 | 50 | 43.2 | 1985 | 51 | 35.9 | 1669 | 62 |
| 70 | 55 | 47.8 | 2183 | 56 | 39.3 | 1820 | 66 |

Figure 10:
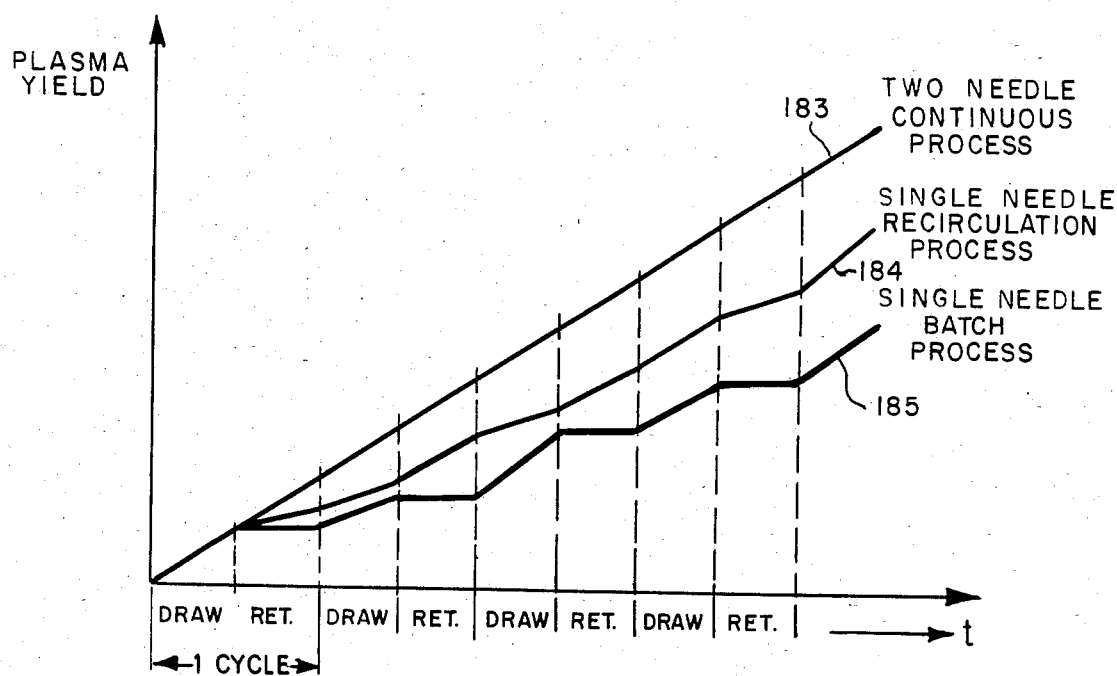
FIG. 10 is a simplified depiction of collected plasma volume versus time for various types of blood fractionation systems useful in comparing the systems.

Thus, for hematocrits within the normally encountered range of 40–55% the single-lumen single needle partial-recirculation blood fractionation system of the present invention requires less processing time and less whole blood than a non-recirculation single-lumen single needle batch system wherein whole blood is drawn, filtered and returned in discrete batches and no recirculation through the filter takes place. Only the more complex and less convenient two needle continuous flow systems, which requires two phlebotomy needles, has a greater system efficiency. This is illustrated in FIG. 10, wherein collected plasma volumes 183, 184 and 185 are depicted for two needle continuous, single needle recirculation and single needle batch systems, respectively.

duit segment 27 is clamped shut and pumps 32, 40 and 46 are operated to pump saline solution from container 52 and ACD solution from continer 36 throughout the system. Trapped air and bubbles are forced into the combined bubble trap and fluid absence detector 47, wherein they are collected and discharged through line 53 to saline container 52. Fluid absence detector 47 is disabled and the procedure continues until all trapped air has been exhausted. The procedure is then terminated by the operator, and after the system has been connected to the donor, an appropriate input is applied to control circuit 81 to initiate a draw cycle.

Thus, the blood fractionation system of the invention can be conveniently set up, and once in use can operate automatically without continuous operator intervention. By reason of its increased plasma separation efficiency, the system of the invention can utilize a smaller volume filter component and hence a smaller volume flow system, to accomplish a given blood fractionation procedure. Since the smaller filter requires a smaller microporous filter element, the cost of the filter component, and hence the cost of the system, is reduced.

Figure 11:
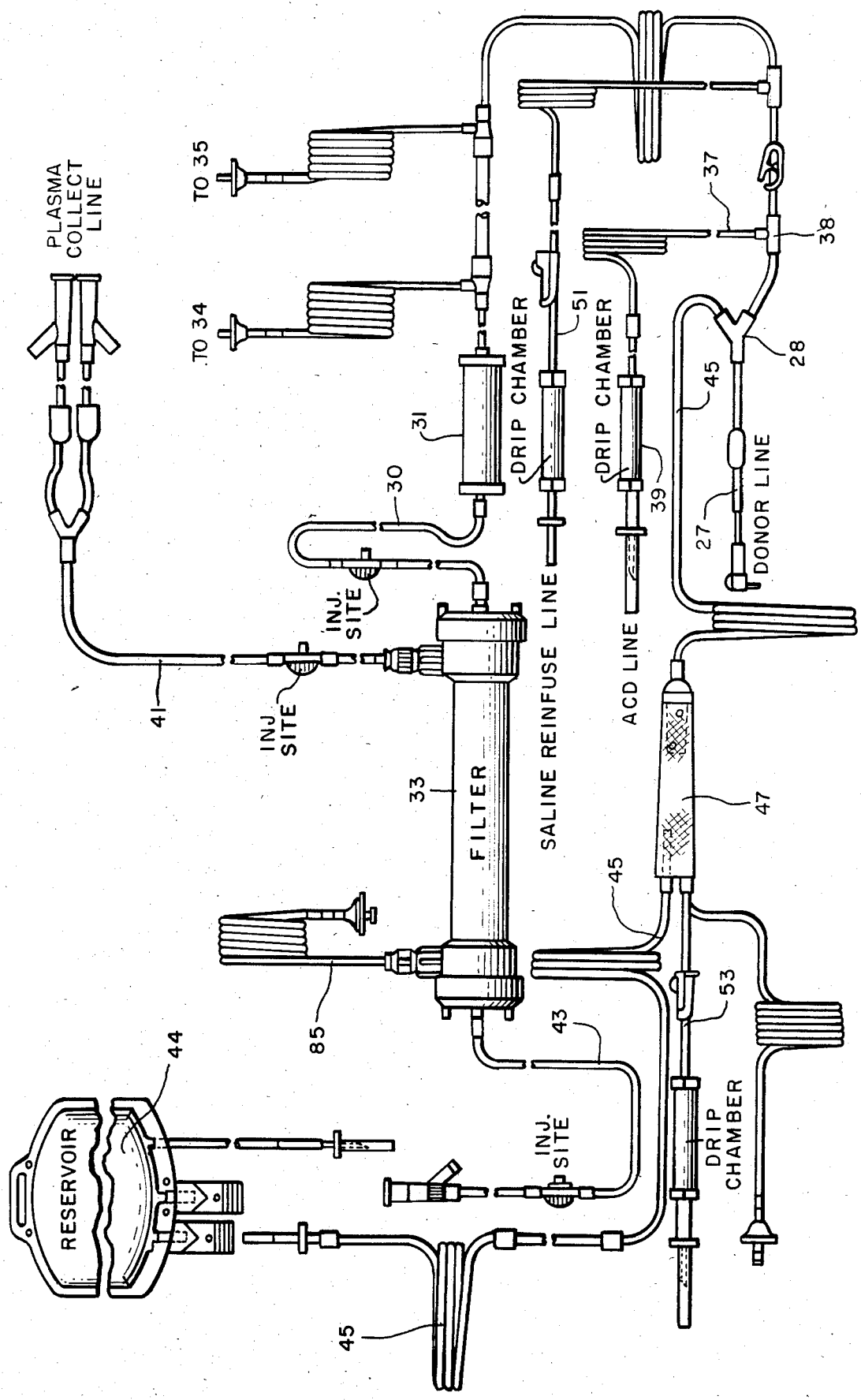
FIG. 11 is a top plan view of a disposable fluid circuit for use in conjunction with the blood fractionation system of the invention.

The fluid flow system 25 utilized in conjunction with the system may be formed of vinyl and other plastic non-pyrogenic materials as a single use disposable flow set, as shown in FIG. 11. The set is preferably individually packaged in a sterile condition for convenient long term storage prior to use.

The mixing chamber 31 is provided up-line of filter 33 to mix the plasma-deficient whole blood diverted for recirculation with previously drawn whole blood, thereby averaging the hematocrit of whole blood circulating through the filter over successive draw and return cycles and enabling the flow rate and pressure at the filter to be more nearly optimized. To this end, the mixing chamber preferably has a volume substantially equal to or greater than the volume of plasma-deficient whole blood pumped from reservoir 44 during the return cycle. This assures that the recirculated plasma-deficient blood will mix with at least an equal volume of previously pumped blood. In practice the mixing chamber may have a volume which is a multiple of the volume pumped from the in-process chamber. For example, in one successful application of the invention, which utilized an intermediate fluid reservoir having a volume of 100 ml., a high limit of 50 ml., and a low limit of 30 ml., a mixing chamber having a volume of 50 ml. was provided in conjunction with a filter having a 5 ml. volume. In this application, a return pump speed of 200 ml/min. was utilized in conjunction with inlet pump pump speeds of 50-70 ml./min. This provided a ratio of 3:1 between the pump speeds, which has been found to provide good efficiency with the 40-55% hematocrit levels typically encountered, as shown in the previous tabulation.

While the use of a weight-responsive transducer has been shown for controlling the return cycle, it is possible to use other control means, such as electrical switches actuated by a mechanical weight scale linkage on which reservoir 44 is supported, or a pair of ultrasonic level detectors arranged to sense blood level in the reservoir. Also, the system may be used in conjunction with a pressure cuff, as described in the copending application of Arnold C. Bilstad et al., "Single Needle Blood Fractionation System Having Pressure Cuff Draw Mode Enhancement", Ser. No. 498,583, now U.S. Pat. No. 4,498,983 filed concurrently herewith.

The blood processing system of the invention has the further advantage of being dependent only on the volume of separated cellular component, or plasma-deficient whole blood, which is directly related to the volume of whole blood processed; and not on the volume of the collected non-cellular component, or plasma, which is dependent on the hematocrit of the whole blood and therefore not directly related to processed volume. This enables the system to draw and return without readjustment batches of uniform volume from different donors, notwithstanding differences in hematocrits between the donors.

While the invention has been shown in conjunction with a hollow fiber type filter, it will be appreciated that it can be utilized in conjunction with other types of filters, such as a flat membrane type filter, or a centrifugal separator. Also, in conjunction with the hollow fiber membrane filter shown, a pressure regulator valve and TMP monitoring system may be employed for more accurate TMP control.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. A single needle blood fractionation system for separating a blood fraction from whole blood, comprising:

means including a donor interface conduit adapted for connection to a single lumen phlebotomy needle and alternately accommodating forward and reverse flow for alternately receiving and returning blood from a donor through the single lumen of the needle;

means including a first conduit communicating with said donor interface conduit, a flow-through filter in said first conduit for separating blood flowing through said filter into a desired blood fraction component and a fraction-depleted blood component, means including an intermediate fluid reservoir for receiving the fraction-depleted blood component from said flow-through filter, and an inlet pump for pumping fluid from said donor interface conduit, through said filter, and into said intermediate reservoir;

means including a second conduit connecting said intermediate fluid reservoir and said donor interface conduit; and a return pump for pumping fluid from said intermediate reservoir through said second conduit;

system control means including means continuously operating said inlet pump at a preselected rate for continuously pumping blood through said first conduit, into said filter and into said reservoir, and means intermittently operating said return pump at a preselected rate for intermittently pumping a predetermined aliquot of the fraction-depleted blood component from said reservoir through said second conduit and into said donor interface conduit, said return pump control means being operative for initiating operation of said return pump when said volume of the fraction-depleted blood component present in said reservoir reaches a predetermined maximum level, and for terminating operation of said return pump when said volume present in said reservoir reaches a predetermined minimum level; and the preselected rate of said intermittently operable return pump being greater than the preselected rate of said continuously operable inlet pump to return during the period said return pump is being operated, a first portion of the predetermined fraction-depleted blood component aliquot to the donor through said donor interface conduit while recirculating a second portion of the predetermined fraction-depleted blood component aliquot through said first conduit, into said filter and into said reservoir along with the whole blood which is being continuously advanced by said inlet pump.

2. A blood fractionation system as defined in claim 1 wherein said system control means are responsive to the weight of said intermediate reservoir.

3. A blood fractionation system as defined in claim 2 wherein said system control means include an electrical weight transducer providing an output signal indicative of the weight of said reservoir.

4. A blood fractionation system as defined in claim 3 wherein said output signal is an analog signal, and said system control means include means for comparing said output signal with predetermined maximum and minimum reference levels.

5. A blood fractionation system as defined in claim 1 wherein the rates of said inlet and return pumps are operator-adjustable.

6. A blood fractionation system as defined in claim 1 wherein said inlet and return pumps are each peristaltic-type pumps.

7. A blood fractionation system as defined in claim 1 wherein said filter is a membrane type filter.

8. A blood fractionation system as defined in claim 7 wherein said filter is a hollow fiber type filter.

9. A blood fractionation system as defined in claim 1 wherein said second fluid conduit means include a bubble trap and a fluid absence detector.

10. A blood fractionation system as defined in claim 1 wherein said separated blood fraction comprises plasma.

11. A blood fractionation apparatus as defined in claim 1 wherein said inlet pump and said return pump each comprise positive displacement pumps.

12. A blood fractionation system as defined in claim 1 and further including means for defining an inline mixing chamber disposed in said first conduit between said donor interface conduit and said flow-through filter, said chamber having a volume substantially equal to or greater than said volume of the fraction-depleted blood component intermittently pumped from said intermediate reservoir to mix said second portion of fraction-depleted blood component recirculated through said first conduit with a portion of whole blood advanced through said first conduit prior to initiating operation of said return pump.

13. The method of separating a blood component from whole blood, utilizing a single lumen phlebotomy needle, and flow-through blood separating means, comprising the steps of:
   continuously pumping in whole blood drawn from a donor through the single lumen of the needle through the separation means to continuously separate the blood into a desired blood fraction component and a fraction-depleted blood component;
   continuously collecting the fraction-depleted blood component from the separation means in a reservoir;
   intermittently pumping back a volume of the fraction-depleted blood component from the reservoir toward the single lumen needle by initiating said pumping back step when the volume of the fraction-depleted blood component in the reservoir rises above a predetermined maximum level and by terminating said pumping back step when the volume of the fraction-depleted blood component in the reservoir returns to a predetermined minimum level; and
   maintaining said pumping back step at a higher rate than said pumping in step to return, during said pumping back step, a first portion of the intermittently pumped volume of the fraction-depleted blood component to the donor through the single lumen needle while recirculating a second portion of the intermittently pumped volume of the fraction-depleted blood component back through the separation means along with the whole blood which is being continuously pumped therethrough.

14. A method as defined in claim 13 and further including the step of
   mixing, prior to its recirculation through the separation means, the second portion of the intermittently pumped volume of the fraction-depleted blood component with a quantity of whole blood drawn from the donor which is substantially equal to or greater in volume than the total volume of the fraction-depleted blood component pumped from the reservoir during said pumping back step.

* * * * *